United States Patent [19]

Itoh et al.

[11] Patent Number: 4,983,633

[45] Date of Patent: Jan. 8, 1991

[54] AMIDE COMPOUNDS, PROCESS FOR PREPARING THE SAME, AND COMPOSITION FOR ACTIVATING GASTRIC MOTOR FUNCTION CONTAINING THE SAME

[75] Inventors: Yasuo Itoh, Katsuyamashi; Hideo Kato, Fukuishi; Eiichi Koshinaka, Katsuyamashi; Nobuo Ogawa, Katsuyamashi; Hiroyuki Nishino, Katsuyamashi; Jun Sakaguchi, Katsuyamashi, all of Japan

[73] Assignee: Hokuriku Pharmaceutical Co., Ltd., Katsuyamashi, Japan

[21] Appl. No.: 241,028

[22] Filed: Sep. 2, 1988

[30] Foreign Application Priority Data

Sep. 5, 1987 [JP] Japan ................................ 62-221211
Sep. 22, 1987 [JP] Japan ................................ 62-236250
Sep. 29, 1987 [JP] Japan ................................ 62-242765
Oct. 5, 1987 [JP] Japan ................................ 62-249749

[51] Int. Cl.$^5$ ................. C07C 233/73; C07C 233/78; A61K 31/165
[52] U.S. Cl. ..................................... 514/622; 514/321; 514/331; 514/422; 514/428; 514/452; 514/618; 514/621; 564/179; 564/162; 564/163; 564/168; 564/166; 546/197; 546/234; 548/526; 548/578; 549/405
[58] Field of Search ............... 564/166, 179, 168, 162, 564/163; 514/619, 321, 315, 331, 422, 428, 452, 622, 618, 621; 548/526, 578; 546/197, 234; 549/405

[56] References Cited

U.S. PATENT DOCUMENTS 3,219,528 11/1965 Thominet ........................... 514/619

FOREIGN PATENT DOCUMENTS 6505819 11/1965 Netherlands .

OTHER PUBLICATIONS

CA. Abstr 17500 (a–e) vol. 64, 1966 of Neth Appl. 6,505,819.

Primary Examiner—Robert A. Wax
Assistant Examiner—Frederick F. Tsung
Attorney, Agent, or Firm—Gordon W. Hueschen

[57] ABSTRACT

Amide-compounds represented by the formula (I):

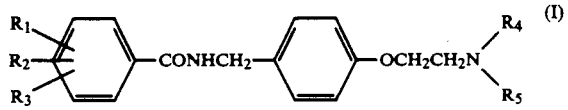

wherein $R_1$ represents hydrogen, lower alkoxy, hydroxy, lower alkyl, halogen, amino which can be substituted by lower alkyl, nitro, cyano, sulfamoyl which can be substituted by lower alkyl, $R_2$ represents hydrogen, lower alkoxy, hydroxy, lower alkyl, halogen, amino, nitro, wherein $R_1$ and $R_2$ can be combined to form methylenedioxy, $R_3$ means hydrogen, lower alkyl, halogen, or amino, $R_4$ and $R_5$ may be the same or different and each represents lower alkyl or wherein $R_4$ and $R_5$ may be combined together with nitrogen to form 1-pyrrolidinyl or piperidino, and pharmacologically-acceptable acid-addition salts thereof, which exhibit excellent effects in the activation of gastric motor function, a process for preparation pharmaceutical compositons thereof, as well as a method for the treatment of a subject suffering from an ailment associated with inadequate gastric motor function by administrating such a compound to the said subject, are all disclosed.

14 Claims, No Drawings

AMIDE COMPOUNDS, PROCESS FOR PREPARING THE SAME, AND COMPOSITION FOR ACTIVATING GASTRIC MOTOR FUNCTION CONTAINING THE SAME

BACKGROUND OF THE INVENTION

1. Field of the Invention

The present invention relates to novel amide compounds represented by the following general formula (I) as well as acid addition salts thereof, process for preparing the same, and a composition for activating gastric motor function containing the same as active ingredient which can be used in the treatment of related ailments.

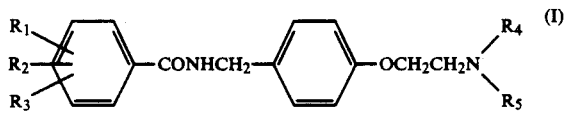

2. Description of the Prior Art

It is already known that N-[4-[2-(dimethylamino)ethoxy]benzyl]-3,4,5-trimethoxybenzamide [general name, TRIMETHOBENZAMIDE, The United States Pharmacopeia XXI, 1094 (1985)] represented by formula (II),

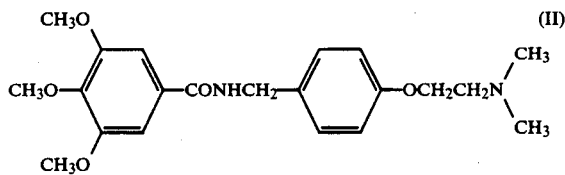

can be used only as an antiemetic drugs and is not used for activating gastric motor function.

Non-ulcer dyspepsia such as gastric discomfort and abdominal distension results in part from a decrease of gastric motor function. Therefore, it is necessary to administer a drug which has the action on activating gastric motor function, so that such symptons can also be alleviated.

So far, as a medicament which has the action on activating gastric motor function, 4-Amino-5-chloro-N-[(2-diethylamino)ethyl]-2-methoxybenzamide (general name, Metoclopramide, The Merck Index 10th Edition, 6019) represented by formula (III) is known.

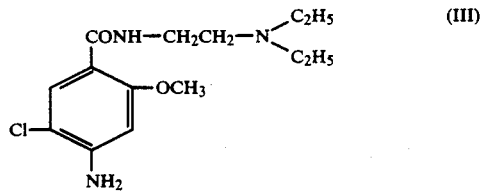

But this medicament has also the antiemetic effect. Medicaments such as this one are not satisfactory for practical use because of insufficient efficacy and having the serious side effects.

Accordingly, there has been a need for a new and useful medicament for the activation of the gastric motor function.

3. Summary of the Invention

It has been found surprisingly, that the amide compounds represented by the formula (I):

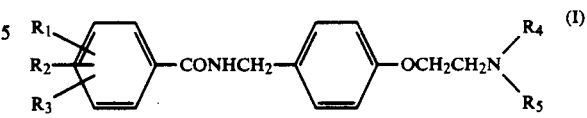

wherein $R_1$ represents hydrogen, lower alkoxy, hydroxy, lower alkyl, halogen, amino which can be substituted by lower alkyl, nitro, cyano, sulfamoyl which can be substituted by lower alkyl, $R_2$ represents hydrogen, lower alkoxy, hydroxy, lower alkyl, halogen, amino, nitro, wherein $R_1$ and $R_2$ can be combined to form methylenedioxy, $R_3$ means hydrogen, lower alkyl, halogen, or amino, $R_4$ and $R_5$ may be the same or different and each represents lower alkyl or wherein $R_4$ and $R_5$ may be combined together with nitrogen to form 1-pyrrolidinyl or piperidino, and pharmacologically-acceptable acid-addition salts thereof, exhibit excellent effects in the activation of gastric motor function.

Further, according to the present invention, there are provided also a process for preparation of the novel amide compounds represented by the general formula (I), pharmaceutical compositions useful to activate gastric motor function comprising one or more compounds as represented by the formula (I) in an amount effective for such purpose, as well as a method for the treatment of a subject suffering from an ailment associated with inadequate gastric motor function by administrating such a compound to the said subject.

DETAILED DESCRIPTION OF THE INVENTION

By the term "lower" in formula (I) is meant a straight or branched carbon chain having 1–4 carbon atoms, inductively. Therefore the lower alkyl moiety of the lower alkyl group encompassed by $R_1$, $R_2$, $R_3$, $R_4$ and $R_5$ is representatively methyl, ethyl, n-propyl, isopropyl, n-butyl, isobutyl, sec-butyl, tert-butyl, etc. The lower alkoxy moiety of the lower alkoxy group is representatively methoxy, ethoxy, n-propoxy, isopropoxy, n-butoxy, etc. As halogen represented by $R_1$, $R_2$ and $R_3$ can be used: fluorine, chlorine and bromine, etc. Examples of amine, which may be substituted by lower alkyl are amino, methylamino, dimethylamino, and diethylamino, etc. and examples of sulfamoyl group, which may be substituted by lower alkyl are sulfamoyl, methylaminosulfonyl and dimethylaminosulfonyl, etc.

The compounds represented by the formula (I) can be converted to their pharmacologically-acceptable acid-addition salts in the usual manner and the free base can be liberated from the resulting salts if desired.

Pharmacologically-acceptable acid-addition salts of the amide compounds represented by the formula (I) include, for example, mineral salts such as hydrochloride, hydrobromide, nitrate, sulfate, phosphate, and the like, or organic acid salts such as acetate, maleate, fumarate, citrate, oxalate, lactate, malate, tartarate, and the like.

The novel amide-compounds represented by the general formula (I) can be prepared as follows:

A functional derivative such as the chloride or other halide, the anhydride or a mixed anhydride, of a carboxylic acid represented by the formula (IV)

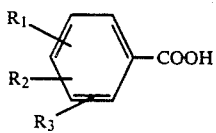

wherein $R_1$, $R_2$ and $R_3$ each has the same meaning as described above, is reacted with an amino-compound represented by the formula (V)

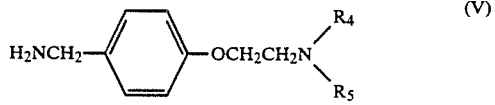

wherein $R_4$ and $R_5$ each has the same meaning as described above, in the presence or absence of a base and in the presence of an inert organic solvent.

Bases which can be used in this method are, for example, pyridine, picoline, lutidine, collidine, N-methylpiperidine, N-methylpyrrolidine, N-methylmorpholine, triethylamine, potassium carbonate, sodium carbonate, or the like.

The solvent used in this reaction can be any kind of solvent which does not inhibit the reaction. Examples of the inert organic solvent which may be used are ether, benzene, toluene, ethyl acetate, tetrahydrofuran, dioxane, chloroform, methylenechloride, dimethylsulfoxide, and N,N-dimethylformamide.

The reaction is generally carried out at a temperature within the range of 0° C. to the reflux temperature of the reaction solvent employed.

The starting materials represented by the above formula (V), most of which are novel compounds, can be prepared by a process shown in the following scheme:

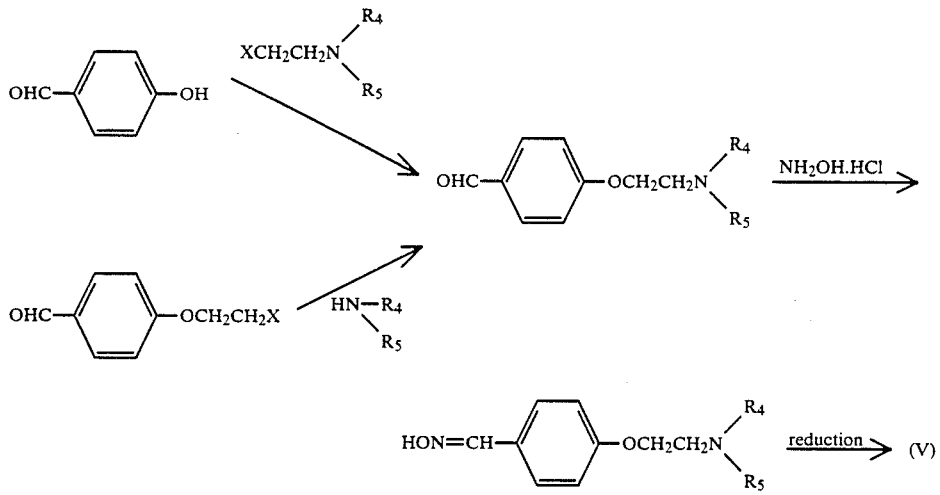

wherein $R_4$ and $R_5$ each has the same meaning as described above and X represents a halogen.

The most important compounds of this invention are for example as follows:

N-[4-[2-(dimethylamino)ethoxy]benzyl]-3,4-dimethoxybenzamide, N-[4-[2-(dimethylamino)ethoxy]benzyl]-3,4-dimethoxybenzamide hydrochloride, 3,4-Methylenedioxy-N-[4-[2-(1-pyrrolidinyl) ethoxy]benzyl] benzamide, 3,4-Dimethoxy-N-[4-[2-(1-pyrrolidinyl) ethoxy]benzyl]benzamide, N-[4-[2-(dimethylamino)ethoxy]benzyl]-4-ethoxy-3-methoxybenzamide, N-[4-[2-(dimethylamino)ethoxy]benzyl]-2-methoxy-5-sulfamoylbenzamide, and 4-amino-5-chloro-2-methoxy-N-[4-[2-(1-pyrrolidinyl) ethoxy]benzyl] benzamide.

A compound of the present invention represented by general formula (I) can be administrated per os, e.g., in the form of pills or tablets, in which it may be present together with any of the usual pharmaceutical carriers, conventionally by compounding a compound of this invention together with a customary carrier or adjuvant, such as talc, magnesium stearate, starch, lactose, gelatin, any of numerous gums, or the like. Thus, in their most advantageous form, the compositions of this invention will contain a non-toxic pharmaceutical carrier in addition to the active ingredient of the present invention. Exemplary solid carriers are lactose, magnesium stearate, calcium stearate, starch, D-mannitol, crystalline cellulose, or the like. Representative liquid carriers are water, sesame oil, olive oil, propylane glycol, or the like. The active agents of this invention can be conveniently administered in such compositions containing active ingredient so as to be within the dosage range illustrated hereinafter. Thus, a wide variety of pharmaceutical forms suitable for many modes of administration and dosages may be employed. For oral administration, the active ingredient and pharmaceutical carrier may, for example, take the form of a powder, granule, pill, tablet, capsule, lozenge, elixir, syrup, or other liquid suspension or emulsion whereas, for parenteral administration, the composition may be in the form of a sterile solution. For intra-rectal administration, the composition may be in the form of a suppository.

The method of using the compounds of this invention comprises internally or externally administering a compound of this invention, preferably orally or parenterally and preferably admixed with the pharmaceutical carrier, for example, in the form of any of the above compositions, or filled into a capsule, to alleviate conditions to be treated and symptoms thereof in a living animal body. Illustratively, it may be used in an amount of about 1.0 to about 1000 mg per day for oral administration, and about 1.0 to about 500 mg per day for a parenteral administration. The unit dose is preferably given a suitable number of times daily, typically three times.

The unit dose may vary depending upon the number of times given in any time period. Naturally, a suitable clinical dose must be adjusted in accordance with the condition, age, and weight of the patient, and it goes without saying that the enhanced activities of the compounds of the invention, together with their reduced side effects, also make them suitable for wide variations, and this invention therefore should not be limited by the exact ranges stated. The exact dosage, both unit dosage and daily dosage, will of course have to be determined according to established medical principles.

The following experiments show with the excellent effect of the present compounds (Compound No. means Example Compound No.), while using metoclopramide hydrochloride (III HCl) and trimethobenzamide hydrochloride (II HCl) as reference compounds.

Experiment 1
Contractile effects of the test compounds in isolated guinea pig ileum Male Hartley guinea-pigs weighing about 450 g were sacrificed and the ileum was excised. Then intact strips 1.5–2.0 cm long were prepared. These preparations were suspended vertically in an organ bath filled with Krebs-Henseleit's solution at 37° C. which was gassed with 95% $O_2$ and 5% $CO_2$. Rhythmic contractions of the preparations were isotonically measured. Effects of the test compounds were assessed as the relative percentage of a test compound against $10^{-6}$M acetylcholine-induced contractions. Results were as follows (Table 1).

TABLE 1

| Test compounds | $ED_{50}$ (M)* |
|---|---|
| Compound 2 | $6.0 \times 10^{-7}$ |
| Compound 3 | $4.6 \times 10^{-7}$ |
| Compound 5 | $1.8 \times 10^{-7}$ |
| Compound 6 | $4.0 \times 10^{-7}$ |
| Compound 7 | $3.0 \times 10^{-7}$ |
| Compound 8 | $1.6 \times 10^{-6}$ |
| Compound 14 | $6.9 \times 10^{-7}$ |
| Compound 19 | $4.2 \times 10^{-7}$ |
| Compound 20 | $5.0 \times 10^{-7}$ |
| Compound 23 | $3.0 \times 10^{-7}$ |
| Compound 24 | $6.1 \times 10^{-7}$ |
| Compound 25 | $6.8 \times 10^{-7}$ |
| Compound 31 | $4.2 \times 10^{-7}$ |
| Compound 32 | $1.4 \times 10^{-7}$ |
| Compound 34 | $1.2 \times 10^{-7}$ |
| Compound 35 | $4.9 \times 10^{-7}$ |
| Compound 36 | $3.4 \times 10^{-7}$ |
| Compound 37 | $1.8 \times 10^{-7}$ |
| Compound 38 | $3.5 \times 10^{-7}$ |
| Compound 39 | $3.9 \times 10^{-7}$ |
| Compound 40 | $6.0 \times 10^{-7}$ |
| Compound 41 | $1.3 \times 10^{-7}$ |
| Compound 42 | $<10^{-7}$ |
| Compound 43 | $<10^{-7}$ |
| Compound 45 | $4.6 \times 10^{-6}$ |
| Compound 47 | $3.0 \times 10^{-6}$ |
| Compound 48 | $5.1 \times 10^{-7}$ |
| Compound 51 | $6.1 \times 10^{-7}$ |
| Compound 52 | $4.5 \times 10^{-7}$ |
| Compound 53 | $4.6 \times 10^{-7}$ |
| Compound 55 | $1.3 \times 10^{-6}$ |
| Compound 56 | $3.2 \times 10^{-7}$ |
| Compound 57 | $9.3 \times 10^{-7}$ |
| Compound 58 | $4.2 \times 10^{-7}$ |
| Compound 59 | $6.2 \times 10^{-7}$ |
| Compound 62 | $3.9 \times 10^{-7}$ |
| Compound 63 | $5.0 \times 10^{-7}$ |
| Metoclopramide HCl | $6.3 \times 10^{-6}$ |
| Trimethobenzamide HCl | $1.5 \times 10^{-6}$ |

*The dose which evoked 50% of the acetylcholine-induced contraction.

These results showed that compound 2 had about 10 times and about 2.5 times stronger contractile effect than metoclopramide.HCl and trimethobenzamide.HCl respectively.

Experiment 2
Improving effects of the test compound on dopamine-induced suppression of gastrointestinal transit in mice Male mice of the ddY strain weighing about 22 g were fasted overnight and the test compounds (suspended in 0.5% carboxymethylcellulose) were administered orally. Thirty minutes later dopamine (2 mg/kg dissolved in saline) or saline only was administered intraperitoneally followed immediately by the oral administration of charcoal meal (5% charcoal powder suspended in 10% gum arabic). Twenty minutes later the animals were sacrificed and the digestive tracts were isolated from the stomach to the cecum. The gastrointestinal transit was determined by calculating the total intestinal length between the pylorus and the cecum and the length over which charcoal meal was carried from the pylorus. Statistical analysis was carried out by Student's t-test for unpaired observations. Results were as follows (Table 2).

TABLE 2

| Experimental group | Dose (mg/kg, p.o.) | n | Gastrointestinal transit (% ± S.E.) | Improvement (%) |
|---|---|---|---|---|
| Control | — | 10 | 53.3 ± 2.0** | |
| Dopamine alone | — | 12 | 31.7 ± 3.2 | |
| Compound 2 + Dopamine | 30 | 11 | 43.9 ± 2.8** | 56.5 |
| Control | — | 11 | 53.3 ± 2.0** | |
| Dopamine alone | — | 12 | 31.7 ± 3.2 | |
| Compound 3 + Dopamine | 30 | 10 | 44.0 ± 4.7* | 56.9 |
| Control | — | 10 | 50.1 ± 3.0** | |
| Dopamine alone | — | 10 | 25.0 ± 3.4 | |
| Compound 18 + Dopamine | 30 | 10 | 43.0 ± 6.5* | 71.7 |
| Control | — | 12 | 51.8 ± 1.7** | |
| Dopamine alone | — | 13 | 35.9 ± 2.1 | |
| Compound 31 + Dopamine | 30 | 12 | 45.2 ± 3.0* | 58.5 |
| Control | — | 10 | 54.5 ± 3.4** | |
| Dopamine alone | — | 10 | 32.9 ± 3.1 | |
| Compound 34 + Dopamine | 30 | 11 | 46.6 ± 3.4* | 63.4 |
| Control | — | 22 | 50.9 ± 2.1** | |
| Dopamine alone | — | 22 | 32.1 ± 2.0 | |
| Metoclopramide .HCl + Dopamine | 30 | 9 | 37.2 ± 3.2 | 27.1 |
| Control | — | 22 | 50.9 ± 2.1** | |
| Dopamine alone | — | 22 | 32.1 ± 2.0 | |
| Trimethobenzamide .HCl + Dopamine | 30 | 13 | 38.2 ± 3.8 | 32.4 |

* and **: Significantly different from groups treated with dopamine at $P < 0.05$ and $P < 0.01$, respectively.

It is concluded that the compounds of this invention showed significant improvement of gastrointestinal transit which was inhibited by dopamine at a dose of 30 mg/kg, but that the antiemetic drugs both metoclopramide.HCl and trimethobenzamide.HCl did not so only to a much lesser extent.

Experiment 3
Suppressing effects of the test compounds on apomorphine-induced emesis in beagle dogs Male beagle dogs weighing about 8 kg were fasted overnight. The test compounds (suspended or dissolved in 0.5% CMC) were administered orally and the dogs fed fortyfive minutes later. Then, fifteen minutes later 100 mg/kg apomorphine (dissolved in saline) was administered subcutaneously and emetic events were observed for sixty minutes.

As a consequence, and as expected the antiemetic drugs metoclopramide HCl and trimethobenzamide.HCl showed the significant antiemetic effect at doses of 1 mg/kg and 30 mg/kg, respectively. The compound 2 shows however slight antiemetic effect at a dose of 30 mg/kg.

Experiment 4

Acute toxicological study in mice

Male ICR mice aged 5 weeks were used for each determination. The test compounds (2-4 different doses) were intravenously administered and $LD_{50}$ values were calculated using the up and down method. Results were as follows (Table 3).

TABLE 3

| Test compounds | $LD_{50}$ (mg/kg) |
| --- | --- |
| Compound 2 | 190.6 |
| Compound 3 | 62.6 |
| Compound 5 | 94.0 |
| Compound 6 | 39.2 |
| Compound 8 | 85.1 |
| Compound 19 | 70.8 |
| Compound 23 | 74.1 |
| Compound 25 | 87.1 |
| Compound 31 | 104.7 |
| Compound 32 | 112.2 |
| Compound 34 | 44.7 |
| Compound 35 | 61.7 |
| Compound 47 | 68.5 |
| Compound 48 | 83.2 |
| Compound 51 | 85.9 |
| Compound 53 | 77.6 |

The following prescriptive examples and examples are given by way illustration only and are not to be construed as limitations of this invention, many variations of which are possible without departing from the scope and apirit thereof.

| Prescriptive Example 1: Capsule Formulation (hard capsule) | |
| --- | --- |
| Compound of Example 2 | 50 mg |
| Lactose | a proper quantity |
| Corn Starch | 20 mg |
| Magnesium Stearate | 1 mg |
| | to 130 mg |

| Prescriptive Example 2: Tablet Formulation | |
| --- | --- |
| Compound of Example 5 | 50 mg |
| Lactose | a proper quantity |
| Corn Starch | 20 mg |
| Magnesium Stearate | 2 mg |
| Hydroxypropylmethyl cellulose | 8 mg |
| Polyethyleneglycol | 1 mg |
| Titanium Oxide | 1 mg |
| | to 210 mg |

| Prescriptive Example 3: Granule Formulation | |
| --- | --- |
| Compound of Example 2 | 100 mg |
| Lactose | a proper quantity |
| D-Mannitol | 500 mg |
| Hydroxypropyl cellulose | 20 mg |
| Talc | 2 mg |
| | to 1000 mg |

| Prescriptive Example 4: Injection Formulation | |
| --- | --- |
| Compound of Example 6 (hydrochloride) | 50 mg |
| Citric acid | 0.5 mg |
| Sodium Hydroxide | a proper quantity |
| Distilled Water for Injection | a proper quantity |
| | to 1 ml |

| Prescriptive Example 5: Suppository Formulation | |
| --- | --- |
| Compound of Example 48 (hydrochloride) | 50 mg |
| Hard Fat | 1250 mg |
| | to 1300 mg |

Reference 1

4-[2-(Dimethylamino)ethoxy] benzaldehyde

To a solution of 61.1 g of p-hydroxybenzaldehyde in 240 ml of N,N-dimethylformamide was added 138 g of potassium carbonate, 80.7 g of 2-dimethylaminoethyl chloride and 30 ml of isopropyl ether. The mixture was stirred at 60° C. for 1.5 hours. After cooling, the reaction mixture was poured into 720 ml of water, and the whole was extracted with chloroform. The chloroform layer was extracted with aqueous hydrochloric acid. The aqueous layer was made alkaline with aqueous sodium hydroxide solution and extracted with ethyl acetate. The extract was washed with water, dried and evaporated. The residue was distilled to give 69.1 g of colorless oil, b.p. 142°-144° C. (4 mmHg).

NMR spectrum $\delta$ (CDCl$_3$)ppm: 2.34 (6H,s), 2.76 (2H,t,J=6 Hz), 4.15 (2H,t,J=6 Hz), 7.02 (2H,d,J=9 Hz), 7.82 (2H,d,J=9 Hz), 9.87 (1H,s).

Reference 2

4-[2-(1-Pyrrolidinyl)ethoxy]benzaldehyde

A mixture of 2.29 g of 4-(2-bromoethoxy)benzaldehyde, 1.42 g of pyrrolidine and 2.07 g of potassium carbonate in 8 ml of N,N-dimethylformamide was stirred at 60° C. for 2 hours. After cooling, water was added and the whole was extracted with ethyl acetate. The ethyl acetate layer was extracted with aqueous hydrochloric acid. The aqueous layer was made alkaline with potassium carbonate and extracted with ethyl acetate. The extract was washed with water, dried and evaporated. The residue was distilled to give 1.72 g of colorless oil, b.p. 170° C. (5 mmHg).

NMR spectrum $\delta$ (CDCl$_3$)ppm: 1.60-2.27 (4H,m), 2.44-2.80 (4H,m), 2.93 (2H,t,J=6 Hz), 4.19 (2H,t,J=6 Hz), 7.01 (2H,d,J=9 Hz), 7.82 (2H,d,J=9 Hz), 9.87 (1H,s).

In the same manner as described in Reference 1 and 2, the compound in Reference 3 was prepared.

Reference 3

4-(2-Piperidinoethoxy)benzaldehyde

Colorless oil, b.p. 160°-162° C. (6 mmHg).

NMR spectrum $\delta$ (CDCl$_3$)ppm: 1.12-1.76 (6H,m), 2.27-2.61 (4H,m), 2.79 (2H,t,J=6 Hz), 4.18 (2H,t,J=6 Hz), 7.00 (2H,d,J=9 Hz), 7.82 (2H,d,J=9 Hz), 9.87 (1H,s).

Reference 4

4-[2-(Dimethylamino)ethoxy]benzaldoxime

A mixture of 154 g of 4-[2-(dimethylamino)ethoxy]- benzaldehyde and 59.9 g of hydroxyamine hydrochloride in 600 ml of ethanol was boiled for 10 minutes. After cooling, the precipitate was filtered to give hydrochloride as pale yellow crystals, m.p. 174°–175° C. These crystals were dissolved in 150 ml of water. The solution was made alkaline with potassium carbonate and extracted with chloroform. The extract was dried and evaporated. The residue was washed with isopropyl ether to give 157 g of colorless crystals, which were recrystallized from ethyl acetate as colorless flakes, m.p. 95°–96° C.

Analysis for $C_{11}H_{16}N_2O_2$: Calculated %: C, 63.44; H, 7.74; N, 13.45. Found %: C, 63.28; H, 7.71; N, 13.37.

In the same manner as described in Reference 4, the compounds in References 5 and 6 were prepared.

Reference 5

4-[2-(1-Pyrrolidinyl)ethoxy]benzaldoxime hydrochloride:

Colorless plates, m.p. 219°–220.5° C. (EtOH).

Analysis for $C_{13}H_{18}N_2O_2$. HCl: Calculated %: C, 57.67; H, 7.07; N, 10.35. Found %: C, 57.57; H, 7.15;: N, 10.25.

Reference 6

4-(2-Piperidinoethoxy)benzaldoxime hydrochloride

Colorless flakes, m.p. 224°–225° C. (EtOH).

Analysis for $C_{14}H_{20}N_2O_2$. HCl: Calculated %: C, 59.05; H, 7.43; N, 9.84. Found %: C, 58.74; H, 7.28; N, 9.64.

Reference 7

4-(2-Piperidinoethoxy)benzylamine

A suspension of 32.3 g of 4-(2-piperidinoethoxy)benzaldoxime in 400 ml of 10% methanolic ammonia was hydrogenated over 3.6 g of Raney nickel catalyst at a pressure of 50 kg/cm$^2$ and at 30° C. The catalyst was filtered off and the filtrate was evaporated. The residue was distilled to give 27.7 g of colorless oil, b.p. 185°–190° C. (6 mmHg).

NMR spectrum δ (CDCl$_3$)ppm: 1.30–1.90 (8H,m), 2.40–2.60 (4H,m), 2.76 (2H,t,J=6 Hz), 3.79 (2H,s), 4.09 (2H,t,J=6 Hz), 6.86 (2H,d,J=9 Hz), 7.21 (2H,d,J=9 Hz).

In the same manner as described in Reference 7, the compounds in References 8 and 9 were prepared.

Reference 8

4-[2-(1-Pyrrolidinyl)ethoxy]benzylamine

Colorless oil, b.p. 163°–165° C. (3 mmHg).

NMR spectrum δ (CDCl$_3$)ppm: 1.53 (2H,br), 1.70–1.90 (4H,m) 2.50–2.75 (4H,m), 2.89 (2H,t,J=6 Hz), 3.79 (2H,s), 4.10 (2H,t,J=6 Hz), 6.88 (2H,d,J=9 Hz), 7.22 (2H,d,J=9 Hz).

Reference 9

4-[2-(Dimethylamino)ethoxy]benzylamine

Colorless oil, b.p. 142°–144° C. (6 mmHg).

NMR spectrum δ (CDCl$_3$) ppm: 1.45 (2H,s), 2.32 (6H,s), 2.71 (2H,t,J=6 Hz), 3.79 (2H,s), 4.05 (2H,t,J=6 Hz), 6.88 (2H,d,J=9 Hz), 7.21 (2H,d,J=9 Hz).

EXAMPLE 1

N-[4-[2-(Dimethylamino)ethoxy]benzyl]-3,4-dimethoxybenzamide

To a cooled solution of 20.0 g of 4-[2-(dimethylamino)ethoxy]benzylamine in 60 ml of toluene was added a solution of 21.7 g of 3,4-dimethoxybenzoyl chloride (which was prepared with 19.7 g of 3,4-dimethoxybenzoic acid and 38.5 g of thionyl chloride in the usual manner) in 60 ml of toluene with stirring. The mixture was stirred at room temperature for 30 minutes. To the mixture was added 120 ml of water and 1 ml of concentrated hydrochloric acid. The aqueous layer was separated, washed with 20 ml of toluene and made alkaline with 20% sodium hydroxide solution to give a precipitate, which was washed with isopropyl ether, of 37.0 g of pale brownish crystals. Recrystallization of the crystals from ethanol and isopropyl ether gave the title compound as colorless needles, m.p. 111°–112° C.

Analysis for $C_{20}H_{26}N_2O_4$: Calculated %: C, 67.02; H, 7.31; N, 7.82. Found %: C, 66.96; H, 7.28; N, 7.78.

EXAMPLE 2

N-[4-[2-(Dimethylamino)ethoxy]benzyl]-3,4-dimethoxybenzamide hydrochloride

A solution of 3.23 g of N-[4-[2-(dimethylamino)ethoxy]benzyl]-3,4-dimethoxybenzamide in ethanol was acidified by the addition of ethanolic hydrogen chloride. The precipitate was filtered and washed with a mixture of ethanol and isopropyl ether to give 3.22 g of pale brownish crystals, which were recrystallized from ethanol as colorless prisms, m.p. 194°–195° C.

Analysis for $C_{20}H_{26}N_2O_4$. HCl: Calculated %: C, 60.83; H, 6.89; N, 7.09. Found %: C, 60.78; H, 6.99; N, 7.05.

EXAMPLE 3

3,4-Methylenedioxy-N-[4-[2-(1-pyrrolidinyl)ethoxy]benzyl]benzamide:

To a cooled solution of 20.0 g of 4-[2-(1-pyrrolidinyl)ethoxy]benzylamine in 30 ml of chloroform was added 17.7 g of 3,4-methylenedioxybenzoyl chloride (which was prepared with 15.9 g of piperonylic acid and 65.3 g of thionyl chloride in the usual manner). The mixture was stirred at room temperature for 20 minutes and the solvent was evaporated. 150 ml of water was added to the residue and the mixture was washed with ethyl acetate. The aqueous layer was made alkaline with potassium carbonate and was extracted with ethyl acetate. The extract was washed with water, dried, and evaporated. The residue was washed with isopropyl ether to give 30.0 g of colorless crystals, which were recrystallized from ethyl acetate as colorless needles, m.p. 93.5°–94.5° C.

Analysis for $C_{21}H_{24}N_2O_4$: Calculated %: C, 68.46; H, 6.57; N, 7.60. Found %: C, 68.44; H, 6.65; N, 7.45.

EXAMPLE 4

2,4-Dimethoxy-N-[4-[2-(1-pyrrolidinyl)ethoxy]benzyl]benzamide

To a cooled suspension of 1.82 g of 2,4-dimethoxybenzoic acid in 10 ml of tetrahydrofuran was added 1.09 g of ethyl chloroformate and 1.01 g of triethylamine. After stirring for 15 minutes, to the mixture was added a solution of 2.00 g of 4-[2-(1-pyrrolidinyl)ethoxy]benzylamine in 5 ml of tetrahydrofuran. The mixture was stirred for 15 minutes and the solvent was evaporated. To the residue was added 10% hydrochloric acid, and the solution was washed with ethyl acetate. The aqueous layer was made alkaline with potassium carbonate and was extracted with ethyl acetate. The extract was washed with water, dried, and evaporated to give 3.31 g of the title compound as a colorless oil.

Mass spectrum: m/z: 384 (M+)

IR spectrum: ν (liquid) cm$^{-1}$: 1648 (c=o)

NMR spectrum: δ (CDCl$_3$) ppm; 1.62–1.97 (4H,m), 2.44–2.76 (4H,m), 2.88 (2H,t,J=6 Hz), 3.84 (3H,s), 3.86 (3H,s), 4.09 (2H,t,J=6 Hz), 4.58 (2H,d,J=5.5 Hz), 6.46 (1H,d,J=2 Hz), 6.59 (1H,dd,J=9,2 Hz), 6.88 (2H,d,J=9 Hz), 7.27 (2H,d,J=9 Hz), 7.99 (1H,br), 8.21 (1H,d,J=9 Hz).

EXAMPLE 5

4-Amino-5-chloro-N-[4-[2-(dimethylamino)ethoxy]benzyl]-2-methoxybenzamide

To a cooled suspension of 2.49 g of 4-amino-5-chloro-2-methoxybenzoic acid in 15 ml of chloroform were successively added dropwise 1.26 g of triethylamine and 1.35 g of ethyl chloroformate with stirring. The mixture was stirred at the same temperature for 30 minutes. Next, to the mixture was added a solution of 2.00 g of 4-[2-(dimethylamino)ethoxy]benzylamine in 10 ml of chloroform with stirring. The mixture was stirred at room temperature for 14 hours and the solvent was evaporated. 10% Hydrochloric acid was added to the residue and the aqueous solution was washed with ethyl acetate. The aqueous layer was made alkaline with potassium carbonate and was extracted with chloroform. The extract was washed with water, dried, and evaporated. The residue was washed with ether to give 3.87 g of slightly brownish crystals, which were recrystallized from ethanol to give colorless needles, m.p. 147°–148° C.

Analysis for C$_{19}$H$_{24}$ClN$_3$O$_3$: Calculated %: C, 60.39; H, 6.40; N, 11.12. Found %: C, 60.28; H, 6.46; N, 11.12.

Further, the free base was converted into the hydrochloride in the usual way using ethanolic hydrogen chloride as in Example 2. Recrystallization of the hydrochloride from ethanol gave colorless needles, m.p. 206.5°–208° C.

Analysis for C$_{19}$H$_{24}$ClN$_3$O$_3$. HCl: Calculated %: C, 55.08; H, 6.08; N, 10.14. Found %: C, 54.86; H, 6.21; N; 9.98.

EXAMPLE 6

N-[4-[2-(Dimethylamino)ethoxy]benzyl]-2-methoxy-5-sulfamoylbenzamide

To a cooled suspension of 14.3 g of 2-methoxy-5-sulfamoylbenzoic acid in 60 ml of tetrahydrofuran were successively added dropwise 6.25 g of triethylamine and 7.45 g of pivaloyl chloride with stirring. The mixture was stirred at the same temperature for 1 hour and then a solution of 10.0 g of 4-[2-(dimethylamino)ethoxy]-benzylamine in 40 ml of tetrahydrofuran was added dropwise with stirring. The mixture was stirred at room temperature for 14 hours and the solvent was evaporated. Hydrochloric acid (10%) was added to the residue and the aqueous solution was washed with ethyl acetate. The aqueous layer was made alkaline with potassium carbonate to give a precipitate, which was washed with water and ethyl acetate, of 16.6 g of colorless crystals. Recrystallization of the crystals from ethanol gave the title compound as colorless needles, m.p. 154°–155° C.

Analysis for C$_{19}$H$_{25}$N$_3$O$_5$S: Calculated %: C, 56.00; H, 6.18; N, 10.31. Found %: C, 55.71; H, 6.21; N, 10.02.

Further, the free base was converted into the hydrochloride in the usual way. Recrystallization of the hydrochloride from methanol gave colorless needles, m.p. 122.5°–123° C.

Analysis for C$_{19}$H$_{25}$N$_3$O$_5$S HCl. 2H$_2$O: Calculated %: C, 47.55; H, 6.30; N, 8.75. Found %: C, 47.47; H, 5.90; N, 8.72.

EXAMPLE 7

N-[4-[2-(Dimethylamino)ethoxy]benzyl]-5-dimethylaminosulfonyl 2-methoxybenzamide To a cooled suspension of 3.20 g of 5-dimethylaminosulfonyl-2-methoxybenzoic acid in 10 ml of tetrahydrofuran were successively added dropwise 1.25 g of triethylamine and 1.34 g of ethyl chloroformate with stirring. The mixture was stirred at the same temperature for 30 minutes and then a solution of 2.00 g of 4-[2-(dimethylamino)ethoxy]benzylamine in 10 ml of tetrahydrofuran was added dropwise with stirring. The mixture was stirred at room temperature for 2 hours and the solvent was evaporated. Hydrochloric acid (10%) was added to the residue and the aqueous solution was washed with ethyl acetate. The aqueous layer was made alkaline with potassium carbonate and was extracted with ethyl acetate. The extract was dried and evaporated. The residue was washed with isopropyl ether to give 4.10 g of colorless crystals, which were recrystallized from a mixture of ethyl acetate and ether to give colorless needles, m.p. 99.5°–100.5° C.

Analysis for C$_{21}$H$_{29}$N$_3$O$_5$S: Calculated %: C, 57.91; H, 6.71; N, 9.65. Found %: C, 57.69; H, 6.82; N, 9.38.

EXAMPLE 8

N-[4-[2-(Dimethylamino)ethoxy]benzyl]-4-sulfamoylbenzamide

To a cooled solution of 1.50 g of 4-[2-(dimethylamino)ethoxy]benzylamine and 0.87 g of triethylamine in 10 ml of chloroform was added 1.87 g of 4-sulfamoylbenzyl chloride, which was prepared from 1.71 g of 4-sulfamoylbenzoic acid with 16.3 g of thionyl chloride in the usual way, with stirring. The mixture was stirred at room temperature for 30 minutes and the solvent was evaporated. Hydrochloric acid (10%) was added to the residue and the aqueous solution was washed with ethyl acetate. The aqueous layer was made alkaline with potassium carbonate and was extracted with ethyl acetate. The extract was washed with water, dried, and evaporated. The residue was washed with ethyl acetate to give 1.19 g of pale yellow crystals, which were recrystallized from ethanol to give colorless crystals, m.p. 173.5°–174.5° C.

Analysis for C$_{18}$H$_{23}$N$_3$O$_4$S: Calculated %: C, 57.28; H, 6.14; N, 11.13. Found %: C, 57.58; H, 6.40; N, 10.95.

EXAMPLE 9

N-[4-[2-(Dimethylamino)ethoxy]benzyl]-4-fluorobenzamide

To a cooled solution of 2.00 g of 4-[2-(dimethylamino)ethoxy]benzylamine and 1.14 g of triethylamine in 10 ml of chloroform was added 1.80 g of 4-fluorobenzoyl chloride, which was prepared from 1.59 g of 4-fluorobenzoic acid with 7.77 g of thionyl chloride. The mixture was stirred for 30 minutes and the solvent was evaporated. Hydrochloric acid (10%) was added to the residue and the aqueous solution was washed with ethyl acetate. The aqueous layer was made alkaline with potassium carbonate and was extracted with ethyl acetate. The extract was washed with water, dried, and evaporated. The residue was washed with n-hexane to give 3.07 g of pale yellow crystals, which were recrystallized from a mixture of ethanol and ether to give colorless needles, m.p. 113°–114.5° C.

Analysis for $C_{18}H_{21}FN_2O_2$: Calculated %: C, 68.34; H, 6.69; N, 8.85. Found %: C, 68.31; H, 6.67; N, 8.73.

Further, the free base was converted into the hydrochloride in the usual way. Recrystallization of the hydrochloride from ethanol gave colorless plates, m.p. 165°–166° C.

Analysis for $C_{18}H_{21}FN_2O_2 \cdot HCl$: Calculated %: C, 61.27; H, 6.28; N, 7.94. Found %: C, 61.18; H, 6.29; N, 7.75.

EXAMPLES 10

2-Amino-N-[4-[2-(dimethylamino)ethoxy]benzyl]benzamide

To a solution of 2.00 g of 4-[2-(dimethylamino)ethoxy]benzylamine in 20 ml of ethyl acetate was added 1.04 g of isatoic anhydride. The mixture was stirred at room temperature for 15 minutes. Hydrochloric acid (10%) was added to the mixture. The aqueous layer was separated, made alkaline with potassium carbonate and extracted with ethyl acetate. The extract was washed with water, dried, and evaporated. Recrystallization of the residue from ethyl acetate gave 1.85 g of colorless pillars, m.p. 104°–105° C.

Analysis for $C_{18}H_{23}N_3O_2$: Calculated %: C, 68.98; H, 7.40; N, 13.41. Found %: C, 69.07; H, 7.03; N, 13.32.

In the same manner as described in Examples 1 to 10, the compounds of Examples 11 to 86 were prepared.

The physical and chemical properties of the compounds of Examples 11 to 86 are shown in Tables 4 and 5.

TABLE 4

R1, R2, R3 — CONHCH2 — C6H4 — OCH2CH2N(R4)(R5)

| Example No. | R1 | R2 | R3 | R4 | R5 | salt | crystals | melting point (solvent) | Analysis for | (Calcd. C;H;N; Found C;H;N;) |
|---|---|---|---|---|---|---|---|---|---|---|
| 11 | 2-OMe | 3-OMe | H | Me | Me | fumarate | colorless needles | 122~123° (EtOH) | $C_{28}H_{26}N_2O_4 \cdot C_4H_4O_4$ | 60.75; 6.37; 5.90  60.62; 6.41; 5.79 |
| 12 | 2-OMe | 4-OMe | H | Me | Me | — | colorless needles | 75~76° (EtOH-iPr2O) | $C_{22}H_{26}N_2O_4$ | 67.02; 7.31; 7.82  67.04; 7.26; 7.57 |
| 13 | 2-OMe | 6-OMe | H | Me | Me | — | colorless plates | 130~131° (AcOEt) | $C_{22}H_{26}N_2O_4$ | 67.02; 7.31; 7.82  66.85; 7.29; 7.58 |
| 14 | 3-OMe | 5-OMe | H | Me | Me | — | colorless needles | 71~72° (EtOH-iPr2O) | $C_{22}H_{26}N_2O_4$ | 67.02; 7.31; 7.82  66.90; 7.12; 7.59 |
| 15 | 3,4—O—CH2—O— | | H | Me | Me | — | colorless crystals | 89~90° (EtOH-iPr2O) | $C_{19}H_{22}N_2O_4$ | 66.65; 6.48; 8.18  66.61; 6.45; 8.03 |
| 16 | " | " | H | " | " | hydrochloride | colorless needles | 166~167° (EtOH) | $C_{19}H_{22}N_2O_4 \cdot HCl$ | 60.24; 6.12; 7.39  60.13; 6.21; 7.16 |
| 17 | 3-OMe | 4-OH | H | Me | Me | — | colorless plates | 129.5~130.5° (AcOEt) | $C_{19}H_{24}N_2O_4$ | 66.26; 7.02; 8.13  66.34; 7.05; 7.97 |
| 18 | 3,4—O—CH2—O— | | H | —(CH2)5— | | — | yellow needles | 64~65° (AcOEt-iPr2O) | $C_{22}H_{26}N_2O_4$ | 69.09; 6.85; 7.32  69.05; 6.74; 7.19 |
| 19 | 3-OMe | 4-OMe | H | —(CH2)4— | | — | colorless needles | 93~95° (AcOEt-iPr2O) | $C_{22}H_{28}N_2O_4$ | 68.73; 7.34; 7.29  68.61; 7.38; 7.09 |
| 20 | 3-OMe | 4-OMe | H | —(CH2)5— | | — | yellow needles | 113~114° (AcOEt-iPr2O) | $C_{23}H_{30}N_2O_4$ | 69.32; 7.59; 7.03  69.49; 7.73; 6.92 |
| 21 | H | H | H | Me | Me | — | colorless plates | 84~85° (iPr2O) | $C_{18}H_{22}N_2O_2$ | 72.46; 7.43; 9.39  72.53; 7.25; 9.34 |
| 22 | 4-OH | H | H | Me | Me | — | colorless scales | 133~134° (EtOH) | $C_{18}H_{22}N_2O_3$ | 68.77; 7.05; 8.91  69.04; 7.15; 8.95 |
| 23 | 2-OMe | H | H | Me | Me | — | colorless needles | 72.5~73.5° (iPr2O) | $C_{19}H_{24}N_2O_3$ | 69.49; 7.37; 8.53  69.40; 7.36; 8.33 |
| " | " | " | " | " | " | hydrochloride | colorless needles | 156.5~157.5° (EtOH) | $C_{19}H_{24}N_2O_3 \cdot HCl$ | 62.54; 6.91; 7.68  62.53; 6.99; 7.38 |
| " | 3-OMe | H | H | " | " | — | colorless needles | 66~68° (iPr2O) | $C_{19}H_{24}N_2O_3$ | 69.49; 7.37; 8.53  69.49; 7.13; 8.44 |
| " | " | " | " | " | " | maleate | colorless plates | 100~101° (iPrOH-iPr2O) | $C_{19}H_{24}N_2O_3 \cdot C_4H_4O_4$ | 62.15; 6.35; 6.30  62.02; 6.26; 6.35 |
| 24 | 4-OMe | H | H | Me | Me | — | colorless needles | 119~120° (EtOH-Et2O) | $C_{19}H_{24}N_2O_3$ | 69.49; 7.37; 8.53  69.47; 7.29; 8.42 |
| " | " | " | " | " | " | hydrochloride | colorless needles | 175~176° (EtOH) | $C_{19}H_{24}N_2O_3 \cdot HCl$ | 62.54; 6.91; 7.68  62.46; 6.97; 7.52 |
| 25 | 4-OEt | H | H | Me | Me | — | colorless needles | 128~129° (AcOEt) | $C_{28}H_{26}N_2O_3$ | 70.15; 7.65; 8.18  69.93; 7.75; 7.94 |

TABLE 4-continued $$\text{structure: } R_1, R_2, R_3 \text{ substituted phenyl-CONHCH}_2\text{-phenyl-OCH}_2\text{CH}_2\text{N}(R_4)(R_5)$$

| Example No. | R₁ | R₂ | R₃ | R₄ | R₅ | salt | crystals | melting point (solvent) | Analysis for | (Calcd. C;H;N;, Found C;H;N;) | |
|---|---|---|---|---|---|---|---|---|---|---|---|
| 26 | 4-OBu-n | " | " | " | " | hydrochloride | colorless scales | 164~165° (EtOH-Et₂O) | C₂₈H₂₆N₂O₃·HCl | 63.40; 7.18; 7.39 | 63.15; 7.32; 7.23 |
| 27 | 4-OMe | H | H | Me | Me | — | colorless scales | 131~132° (AcOEt) | C₂₂H₂₆N₂O₃ | 71.32; 8.16; 7.56 | 71.17; 8.26; 7.53 |
| 28 | 4-OMe | H | H | —(CH₂)₄— | — | colorless needles | 120~121° (AcOEt) | C₂₂H₂₆N₂O₃ | 71.16; 7.39; 7.90 | 70.93; 7.54; 7.97 |
| 29 | 4-OEt | H | H | —(CH₂)₄— | — | colorless prisms | 125~127° (AcOEt) | C₂₂H₂₈N₂O₃ | 71.71; 7.66; 7.60 | 71.57; 7.84; 7.52 |
| 30 | 3-OEt | H | H | Me | Me | — | colorless needles | 80~81° (iPr₂O) | C₂₈H₂₆N₂O₃ | 70.15; 7.65; 8.18 | 70.03; 7.55; 8.09 |
| 31 | 4-OPr-n | H | H | Me | Me | — | colorless prisms | 117~119° (AcOEt) | C₂₂H₂₈N₂O₃ | 70.76; 7.92; 7.86 | 70.58; 7.93; 7.81 |
| 32 | 3-OMe | 4-OEt | H | Me | Me | — | colorless needles | 113~114° (AcOEt) | C₂₁H₂₃N₂O₄ | 97.72; 7.58; 7.52 | 67.66; 7.61; 7.50 |
| 33 | 3-OEt | 4-OEt | H | Me | Me | — | colorless needles | 127.5~129° (AcOEt) | C₂₂H₃₈N₂O₄ | 68.37; 7.82; 7.25 | 68.39; 7.54; 7.11 |
| 34 | 3-OEt | 5-OEt | H | Me | Me | — | colorless needles | 114~114.5° (AcOEt) | C₂₂H₃₆N₂O₄ | 68.37; 7.82; 7.25 | 68.15; 7.73; 7.20 |
| 35 | 2-OMe | 4-NH₂ | 5-Cl | —(CH₂)₄— | — | colorless needles | 144~146.5° (EtOH) | C₂₁H₂₅ClN₃O₃ | 62.45; 6.49; 10.40 | 62.49; 6.56; 10.26 |
| 36 | 2-OMe | 4-NH₂ | 5-Cl | —(CH₂)₅— | — | colorless needles | 121~122° (AcOEt) | C₂₂H₂₈ClN₃O₃ | 63.23; 6.75; 10.05 | 63.24; 6.80; 9.78 |
| 37 | 5-SO₂NHMe | 2-OMe | H | Me | Me | — | colorless needles | 154~156° (AcOEt-EtOH) | C₂₆H₂₇N₃O₅S·½H₂O | 55.80; 6.56; 9.76 | 56.10; 6.61; 9.77 |
| 38 | 5-SO₂NH₂ | 2-OMe | H | —(CH₂)₄— | — | colorless crystals | 91~93° (EtOH) | C₂₁H₂₇N₃O₅S·H₂O | 55.86; 6.47; 9.31 | 55.66; 6.35; 9.06 |
| 39 | 5-SO₂NH₂ | 2-OMe | H | —(CH₂)₅— | — | colorless needles | 113~114° (MeOH) | C₂₂H₂₈N₃O₅S·H₂O | 56.76; 6.71; 9.03 | 56.81; 6.74; 8.84 |
| 40 | " | " | " | " | " | hydrochloride | colorless needles | 203~204° (MeOH) | C₂₂H₂₉N₃O₅S·HCl | 54.09; 6.29; 8.60 | 53.98; 6.28; 8.39 |
| 41 | 3-SO₂N·Me₂ | 4-Cl | H | Me | Me | hydrochloride | colorless needles | 146~147° (EtOH) | C₂₀H₂₅ClN₃O₄S·HCl·½H₂O | 49.49; 5.81; 8.66 | 49.55; 5.83; 8.43 |
| 42 | 3-SO₂N·Me₂ | 4-Cl | H | —(CH₂)₄— | — | fumarate | colorless prisms | 110~111° (EtOH) | C₂₂H₂₈ClN₃O₄S·C₄H₄O₄·½H₂O | 52.83; 5.63; 7.11 | 52.79; 5.64; 6.95 |
| 43 | 5-SO₂NH₂ | 2-OMe | 4-NH₂ | Me | Me | — | colorless needles | 160~161° (EtOH) | C₁₉H₂₅N₄O₅S | 52.89; 6.31; 12.98 | 52.89; 6.23; 12.98 |
| 44 | " | " | " | " | " | hydrochloride | colorless needles | 134~136° (MeOH-AcOEt) | C₁₉H₂₅N₄O₅S·HCl·H₂O | 47.84; 6.13; 11.75 | 48.12; 6.27; 11.50 |
| | 3-SO₂N·Me₂ | 2-OMe | H | —(CH₂)₄— | — | — | colorless prisms | 128~129° (EtOH) | C₂₃H₃₂N₃O₅S | 59.85; 6.77; 9.10 | 59.89; 6.68; 9.10 |
| | 5-SO₂NHMe | 2-OMe | H | —(CH₂)₄— | — | — | colorless scales | 168~169° (EtOH) | C₂₃H₂₉N₃O₅S | 59.04; 6.53; 9.39 | 58.82; 6.24; 9.33 |
| | 2-Cl | H | H | Me | Me | — | colorless needles | 66~67° (iPr₂O) | C₁₈H₂₁ClN₂O₂ | 64.09; 6.42; 8.30 | 64.24; 6.39; 8.07 |
| | " | " | " | " | " | hydrochloride | colorless | 207~209° | C₁₈H₂₁ClN₂O₂·HCl | 58.54; 6.00; 7.59 | 58.30; 6.07; 7.30 |

TABLE 4-continued $$\text{R}_1, \text{R}_2, \text{R}_3\text{-C}_6\text{H}_2\text{-CONHCH}_2\text{-C}_6\text{H}_4\text{-OCH}_2\text{CH}_2\text{N}(\text{R}_4)(\text{R}_5)$$

| Example No. | $R_1$ | $R_2$ | $R_3$ | $R_4$ | $R_5$ | salt | crystals | melting point (solvent) | Analysis for | (Calcd. C;H;N; | Found C;H;N) |
|---|---|---|---|---|---|---|---|---|---|---|---|
| 45 | 3-Cl | H | H | Me | Me | — | colorless scales | 78~79° (EtOH) | $C_{18}H_{21}ClN_2O_2$ | 64.96; 6.36; 7.59 | 65.02; 6.37; 8.18 |
|  | " | " | " | " | " | hydrochloride | colorless needles | 166~167° (iPr$_2$O) | $C_{18}H_{21}ClN_2O_2 \cdot HCl$ | 58.54; 6.00; 7.59 | 58.27; 6.20; 7.26 |
| 46 | 4-Cl | H | H | Me | Me | — | colorless scales | 105~106° (EtOH-Et$_2$O) | $C_{18}H_{21}ClN_2O_2$ | 64.96; 6.36; 7.59 | 65.05; 6.42; 8.24 |
|  | " | " | " | " | " | hydrochloride | colorless scales | 186~188° (EtOH-iPr$_2$O) | $C_{18}H_{21}ClN_2O_2 \cdot HCl$ | 58.54; 6.00; 7.59 | 58.46; 6.21; 7.21 |
| 47 | 3-Me | H | H | Me | Me | hydrochloride | colorless needles | 118~120° (EtOH-Me$_2$CO) | $C_{19}H_{24}N_2O_2 \cdot HCl$ | 65.41; 7.22; 8.03 | 65.25; 7.19; 7.83 |
| 48 | 4-Me | H | H | Me | Me | — | colorless prisms | 109~110° (iPr$_2$O) | $C_{18}H_{24}N_2O_2$ | 73.05; 7.74; 8.97 | 73.16; 7.61; 8.78 |
|  | " | " | " | " | " | hydrochloride | colorless plates | 197~199° (EtOH-Et$_2$O) | $C_{18}H_{24}N_2O_2 \cdot HCl$ | 65.41; 7.22; 8.03 | 65.20; 7.32; 7.70 |
| 49 | 4-Et | H | H | Me | Me | — | colorless pillars | 101~102° (iPr$_2$O) | $C_{18}H_{26}N_2O_2$ | 73.59; 8.03; 8.58 | 73.65; 7.98; 8.38 |
| 50 | 2-NO$_2$ | H | H | Me | Me | hydrochloride | colorless needles | 190~191° (EtOH) | $C_{18}H_{22}N_3O_4 \cdot HCl$ | 56.92; 5.84; 11.06 | 56.91; 6.05; 10.82 |
| 51 | 3-NO$_2$ | H | H | Me | Me | — | pale yellow needles | 88~89° (AcOEt-Et$_2$O) | $C_{18}H_{22}N_3O_4$ | 63.96; 6.16; 12.24 | 62.90; 6.24; 12.18 |
|  | " | " | " | " | " | hydrochloride | colorless needles | 204~205 (EtOH) | $C_{18}H_{22}N_3O_4 \cdot HCl$ | 56.92; 5.84; 11.06 | 56.95; 6.04; 10.79 |
| 52 | 4-NO$_2$ | H | H | Me | Me | — | pale yellow needles | 153~154° (AcOEt) | $C_{18}H_{22}N_3O_4$ | 62.96; 6.16; 12.24 | 62.94; 6.13; 12.18 |
| 53 | 4-CN | H | H | Me | Me | — | pale yellow needles | 93~94° (AcOEt-Et$_2$O) | $C_{18}H_{22}N_3O_2$ | 70.57; 6.55; 12.99 | 70.41; 6.42; 12.71 |
|  | " | " | " | " | " | hydrochloride | pale yellow needles | 182~183° (EtOH) | $C_{18}H_{22}N_3O_2 \cdot HCl \cdot \tfrac{1}{4}H_2O$ | 62.63; 6.22; 11.53 | 62.94; 6.13; 11.25 |
| 54 | 4-tBu | H | H | Me | Me | — | colorless needles | 135~137° (AcOEt) | $C_{22}H_{38}N_2O_2$ | 74.54; 8.53; 7.90 | 74.60; 8.28; 7.86 |
| 55 | 4-N.Me$_2$ | H | H | Me | Me | — | colorless needles | 144~146° (AcOEt) | $C_{28}H_{27}N_3O_2$ | 70.35; 7.97; 12.31 | 70.21; 7.58; 12.02 |
| 56 | 4-Me | H | H | —(CH$_2$)$_4$— | | — | colorless prisms | 105~107° (AcOEt) | $C_{22}H_{28}N_2O_2$ | 74.53; 7.74; 8.28 | 74.63; 7.44; 8.19 |
| 57 | 4-CN | H | H | —(CH$_2$)$_4$— | | — | colorless prisms | 102~103° (AcOEt) | $C_{22}H_{23}N_3O_2$ | 72.18; 6.63; 12.03 | 71.96; 6.49; 11.80 |
| 58 | 3-NO$_3$ | H | H | —(CH$_2$)$_4$— | | hydrochloride | grayish brown needles | 176~178° (EtOH) | $C_{20}H_{23}N_3O_4 \cdot HCl$ | 59.18; 5.96; 10.35 | 58.90; 5.97; 10.39 |
| 59 | 2-Cl | 4-Cl | H | Me | Me | — | colorless needles | 111~112° (C$_6$H$_6$) | $C_{18}H_{20}Cl_2N_2O_2$ | 58.87; 5.49; 7.63 | 58.89; 5.46; 7.51 |
|  | " | " | " | " | " | hydrochloride | colorless scales | 218~219° (EtOH) | $C_{18}H_{20}Cl_2N_2O_2 \cdot HCl$ | 53.55; 5.24; 6.94 | 53.41; 5.39; 6.78 |
| 60 | 3-Cl | 4-Cl | H | Me | Me | hydrochloride | colorless needles | 209.5~212° | $C_{18}H_{20}Cl_2N_2O_2 \cdot HCl$ | 53.55; 5.24; 6.94 | 53.75; 5.47; 6.89 |

TABLE 4-continued

Structure: (R1, R2, R3)-phenyl-CONHCH2-(phenyl-OCH2CH2N(R4)(R5))

| Example No. | R1 | R2 | R3 | R4 | R5 | salt | crystals | melting point (solvent) | Analysis for | (Calcd. C;H;N; Found C;H;N) |
|---|---|---|---|---|---|---|---|---|---|---|
| 61 | 3-Cl | 5-Cl | H | Me | Me | hydrochloride | colorless needles | 159~160° (MeOH) | $C_{18}H_{22}Cl_2N_2O_2 \cdot HCl$ | 53.55; 5.24; 6.94  53.46; 5.46; 6.71 |
| 62 | 3-Me | 4-NO2 | H | Me | Me | — | yellow needles | 88~90° (EtOH) | $C_{19}H_{22}N_3O_4$ | 63.85; 6.49; 11.76  63.56; 6.61; 11.70 |
| "  | "  | "  | "  | "  | "  | hydrochloride | colorless needles | 170~171° (EtOH-Et2O) | $C_{19}H_{22}N_3O_4 \cdot HCl$ | 57.94; 6.14; 10.67  57.66; 6.38; 10.63 |
| 63 | 3-Me | 4-NO2 | H | —(CH2)4— | — | — | pale yellow prisms | 113~114° (AcOEt) | $C_{22}H_{28}N_3O_4$ | 65.78; 6.57; 10.96  65.49; 6.68; 10.87 |
| 64 | 4-Me | H | H | —(CH2)5— | — | — | colorless prisms | 90~91° (iPr2O) | $C_{22}H_{28}N_2O_3$ | 74.97; 8.01; 7.95  74.93; 7.81; 7.85 |
| 65 | 2-OEt | H | H | Me | Me | hydrochloride | colorless needles | 127~130° (EtOH-n-C6H14) | $C_{28}H_{28}N_2O_3 \cdot HCl$ | 63.40; 7.18; 7.39  63.14; 7.32; 7.41 |
| 66 | 2-OH | H | H | Me | Me | hydrochloride | colorless prisms | 153~156° (EtOH) | $C_{18}H_{22}N_2O_3 \cdot HCl$ | 61.62; 6.61; 7.98  61.63; 6.66; 7.95 |
| 67 | 3-OH | H | H | Me | Me | — | colorless plates | 151~153° (EtOH) | $C_{18}H_{22}N_2O_3$ | 68.77; 7.05; 8.91  68.94; 7.21; 8.98 |
| 68 | 3-SO2NH2 | H | H | Me | Me | — | colorless crystals | 169~172° (EtOH) | $C_{18}H_{22}N_3O_4S$ | 57.28; 6.14; 11.13  57.30; 6.07; 11.12 |
| 69 | 2-Me | H | H | Me | Me | hydrochloride | colorless scales | 186~187.5° (EtOH) | $C_{19}H_{24}N_2O_2 \cdot HCl$ | 65.41; 7.22; 8.03  65.34; 7.14; 8.00 |
| 70 | 2-F | H | H | Me | Me | — | colorless needles | 70~72° (AcOEt-n-C6H14) | $C_{18}H_{22}FN_2O_2$ | 68.34; 6.69; 8.85  68.24; 6.57; 8.87 |
| "  | "  | "  | "  | "  | "  | hydrochloride | colorless needles | 139~142° (EtOH-Et2O) | $C_{18}H_{22}FN_2O_2 \cdot HCl$ | 61.27; 6.28; 7.94  61.25; 6.30; 7.97 |
| 71 | 3-F | H | H | Me | Me | — | colorless needles | 86~87° (iPr2O) | $C_{18}H_{22}FN_2O_2$ | 68.34; 6.69; 8.85  68.34; 6.66; 8.83 |
| "  | "  | "  | "  | "  | "  | fumarate | colorless plates | 127~128° (EtOH) | $C_{18}H_{22}FN_2O_2 \cdot C_4H_4O_4$ | 61.10; 5.83; 6.48  60.94; 5.88; 6.55 |
| 72 | 3-NH2 | H | H | Me | Me | hydrochloride | colorless crystals | 173~174° (MeOH-AcOEt) | $C_{18}H_{23}N_3O_2 \cdot 2HCl$ | 55.96; 6.52; 10.88  56.13; 6.49; 10.89 |
| 73 | 4-NH2 | H | H | Me | Me | hydrochloride | colorless needles | 171~173° (MeOH) | $C_{18}H_{23}N_3O_2 \cdot 2HCl$ | 55.96; 6.52; 10.88  55.89; 6.69; 10.88 |
| 74 | 3-CN | H | H | Me | Me | — | colorless crystals | 99~100° (AcOEt-iPr2O) | $C_{18}H_{22}N_3O_2$ | 70.57; 6.55; 12.99  70.65; 6.51; 12.99 |
| "  | "  | "  | "  | "  | "  | hydrochloride | colorless prisms | 155~157° (EtOH) | $C_{19}H_{22}N_3O_2 \cdot HCl$ | 63.42; 6.16; 11.68  63.32; 6.14; 11.73 |
| 75 | 3-tBu | 4-OH | 5-tBu | Me | Me | — | colorless plates | 142~144° (Me2CO-iPr2O) | $C_{26}H_{38}N_2O_3$ | 73.20; 8.98; 6.57  73.47; 8.96; 6.29 |
| 76 | 3-Cl | 4-NH2 | 5-Cl | Me | Me | hydrochloride | pale brown needles | 132~134° (EtOH) | $C_{18}H_{22}Cl_2N_3O_2 \cdot HCl \cdot \tfrac{1}{2}H_2O$ | 50.54; 5.42; 9.82  50.55; 5.51; 9.71 |
| 77 | 3-Cl | 4-NH2 | 5-Cl | —(CH2)4— | — | — | pale brown needles | 63~64° (AcOEt) | $C_{28}H_{23}Cl_8N_3O_2$ | 58.83; 5.68; 10.29  59.00; 6.04; 10.19 |
| 78 | 2-F | 4-F | 5-F | Me | Me | — | colorless prisms | 80~82° (AcOEt) | $C_{18}H_{19}F_3N_2O_2$ | 61.36; 5.44; 7.95  61.32; 5.71; 7.98 |

TABLE 5

Structure:

R1, R2, R3 substituted phenyl—CONHCH2—phenyl—OCH2CH2N(R4)(R5)

| Example No. | R1 | R2 | R3 | R4 | R5 | | Ms spectrum m/z (M) | IR spectrum ν (liq)cm⁻¹ | NMR spectrum δ (CDCl3)ppm |
|---|---|---|---|---|---|---|---|---|---|
| 79 | 3-OMe | H | H | —(CH2)4— | | yellow oil | 354 | 1650 (C=O) | 1.66–1.98(4H, m), 2.44–2.76(4H, m), 2.88(2H, t, J=6Hz), 3.82(3H, s), 4.09(2H, t, J=6Hz), 4.61(2H, d, J=5.5Hz), 6.47(1H, br), 6.97(2H, d, J=9Hz), 7.20–7.38(6H, m) |
| 80 | 3-SO2NH2 | 4-Cl | H | Me | Me | pale yellow oil | 413, 411 (1:3) | 1648 (C=O) | 2.29(6H, s), 2.69(2H, t, J=5.5Hz), 3.92(2H, br), 3.99(2H, t, J=5.5Hz), 4.47(2H, d, J=5.5Hz), 6.78(2H, d, J=9Hz), 7.07(1H, t, J=5.5Hz), 7.49(1H, d, J=8.5Hz), 7.92(1H, dd, J=8.5, 2Hz), 8.32(1H, d, J=2Hz) |
| 81 | 3-SO2NH.Me | 4-Cl | H | Me | Me | colorless oil | 427, 425 (1:3) | 1650 (C=O) | 2.32(6H, s), 2.62(3H, s), 2.71(2H, t, J=5.5Hz), 4.04(2H, t, J=5.5Hz), 4.54(2H, d, J=5.5Hz), 5.88(1H, br), 6.85(2H, d, J=9Hz), 7.25(2H, d, J=9Hz), 7.56(1H, d, J=8.5Hz), 7.99(1H, dd, J=8.5, 2Hz), 8.39(1H, d, J=2Hz) |
| 82 | 3-SO2NH2 | 4-Cl | H | —(CH2)4— | | yellow oil | 439, 437 (1:3) | 1644 (C=O) | 1.55–1.97(4H, m), 2.32–2.72(4H, m), 2.87(2H, t, J=6Hz), 4.07(2H, t, J=6Hz), 4.52(2H, d, J=9Hz), 6.82(2H, d, J=9Hz), 7.09(2H, d, J=9Hz), 7.36(1H, d, J=8.5Hz), 7.70(1H, br), 7.83(1H, dd, J=8.5, 2Hz), 8.34(1H, d, J=2Hz) |
| 83 | 3-SO2NH.Me | 4-Cl | H | —(CH2)4— | | yellow oil | 453, 451 (1:3) | 1644 (C=O) | 1.57–1.98(4H, m), 2.34–2.77(4H, m), 2.88(2H, t, J=5.5Hz), 4.08(2H, t, J=5.5Hz), 4.53(2H, d, J=5.5Hz), 6.84(2H, d, J=9Hz), 7.16(1H, br), 7.25(2H, d, J=9Hz), 7.55(1H, d, J=8.5Hz), 8.03(1H, dd, J=8.5, 2Hz), 8.40(1H, d, J=2Hz) |
| 84 | 3-SO2N.Me2 | 4-OMe | H | Me | Me | colorless oil | 435 | 1644 (C=O) | 2.32(6H, s), 2.71(2H, t, J=5.5Hz), 2.82(6H, s), 3.95(3H, s), 4.04(2H, t, J=5.5Hz), 4.53(2H, d, J=5.5Hz), 6.86(2H, d, J=9Hz), 7.03(1H, d, J=8.5Hz), 7.27(2H, d, J=9Hz), 8.10(1H, dd, J=8.5, 2.5Hz), 8.25(1H, d, J=2.5Hz) |
| 85 | 3-SO2N.Me2 | 4-OMe | H | —(CH2)4— | | pale yellow oil | 461 | 1646 (C=O) | 1.62–1.89(4H, m), 2.45–2.75(4H, m), 2.83(6H, s), 2.89(2H, t, J=6Hz), 3.96(3H, s), 4.10(2H, t, J=6Hz), 4.55(2H, d, J=5.5Hz), 6.88(2H, d, J=9Hz), 7.05(1H, d, J=8.5Hz), 7.27(2H, d, J=9Hz), 8.12(1H, dd, J=8.5, 2Hz), 8.22(1H, d, J=2Hz) |
| 86 | 2-F | 4-F | 5-F | —(CH2)4— | | yellow oil | 378 | 1660 (C=O) | 1.57–2.10(4H, m), 2.48–2.80(4H, m), 2.90(2H, t, J=6Hz), 4.10(2H, t, J=6Hz), 4.48–4.72(2H, m), 6.67–7.14(2H, m), 6.89(2H, d, J=9Hz), 7.25(2H, d, J=9Hz), 7.73–8.13(1H, m) |

What is claimed is:

1. Amide-compound selected from N-[4-[2-(dimethylamino)ethoxyl-benzyl]-3,4-dimethoxybenzamide pharmacologically-acceptable acid-addition salts thereof.

2. A compound of claim 1 which is N-[4-[2-(dimethylamino)ethoxy]-benzyl]-3,4-dimethoxybenzamide.

3. A compound of claim 1 which is N-[4-[2-(dimethylamino)ethoxy]-benzyl]-3,4-dimethoxybenzamide hydrochloride.

4. A pharmaceutical composition useful to activate gastric motor function comprising one or more compounds as claimed in claim 1, in an amount effective for such purpose, together with a compatible, pharmaceutically-acceptable carrier or coating.

5. A pharmaceutical composition useful to activate gastric motor function comprising the compound of claim 2, in an amount effective for such purpose, together with a compatible, pharmaceutically-acceptable carrier or coating.

6. A pharmaceutical composition useful to activate gastric motor function comprising the compound of claim 3, in an amount effective for such purpose, together with a compatible, pharmaceutically-acceptable carrier or coating.

7. A method for the treatment of a subject suffering from an ailment associated with inadequate gastric motor function, comprising the step of administering to the said subject an amount of an amide compound selected from those represented by the formula (I)

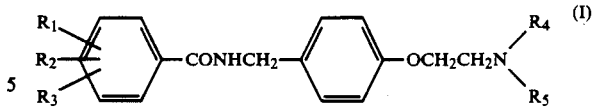

wherein $R_1$ represents hydrogen, lower alkoxy, hydroxy, lower alkyl, halogen, amino which can be substituted by lower alkyl, nitro, cyano, sulfamoyl which can be substituted by lower alkyl, $R_2$ represents hydrogen, lower alkoxy, hydroxy, lower alkyl, halogen, amino, nitro, and wherein $R_1$ and $R_2$ can be combined to form methylenedioxy $R_3$ means hydrogen, lower alkyl, halogen, or amino, and wherein $R_4$ and $R_5$ may be the same or different and each represents lower alkyl and wherein $R_4$ and $R_5$ may be combined together with nitrogen to form 1-pyrrolidinyl or piperidino, and pharmacologically-acceptable acid-addition salts thereof, which is effective for the alleviation of such ailment.

8. Method of claim 7, wherein the compound is N-[4-[2-(dimethylamino)ethoxy]-benzyl]-3,4-dimethoxybenzamide.

9. Method of claim 7, wherein the compound is N-[4-[2-(dimethylamino)ethoxy]-benzyl]-3,4-dimethoxybenzamide hydrochloride.

10. Method of claim 7, wherein the compound is 3,4-Methylenedioxy-N-[4-[2-(1-pyrrolidinyl)ethoxy]-benzyl]benzamide.

11. Method of claim 7, wherein the compound is 3,4-Dimethoxy-N-[4-[2-(1-pyrrolidinyl)ethoxy]benzyl]-benzamide.

12. Method of claim 7, wherein the compound is N-[4-[2-(dimethylamino)ethoxy]-benzyl]-4-ethoxy-3-methoxybenzamide.

13. Method of claim 7, wherein the compound is N-[4-[2-(dimethylamino)ethoxy]-benzyl]-2-methoxy-5-sulfamoylbenzamide.

14. Method of claim 7, wherein the compound is 4-Amino-5-chloro-2-methoxy-N-[4-[2-(1-pyrrolidinyl)ethoxy]benzyl]benzamide.

* * * * *

UNITED STATES PATENT AND TRADEMARK OFFICE
CERTIFICATE OF CORRECTION

PATENT NO. : 4,983,633

DATED : Jan. 8, 1991

INVENTOR(S) : Yasuo Itoh, Hideo Kato, Eiichi Koshinaka, Nobuo Ogawa, Hiroyuki Nishino, Jun Sakaguchi It is certified that error appears in the above-identified patent and that said Letters Patent is hereby corrected as shown below:

Title Page, [57] ABSTRACT, 5th line up from the bottom; "preparation pharmaceutical" should read -- preparation of pharmaceutical --.

Title Page, [57] ABSTRACT, 2nd line up from the bottom; "administrating" should read -- administering --.

Column 1, line 38; "drugs" should read -- drug --.

Column 6, line 56; delete "both".

Column 6, line 57; delete "not"

Column 6, line 65; "fortyfive" should read -- forty-five --.

Column 7, approximately line 33; "way illustration" should read -- way of illustration --.

Column 7, line 36; "apirit" should read -- spirit --.

Column 10, line 37; move the ")" at the beginning of the line to the end of line 36 and delete the hyphen therefrom.

Columns 15 and 16, Table 4, under heading "Analysis for"
  Example No. 11, "$C_{28}$" should read -- $C_{20}$ --.
  Example No. 12, "$C_{28}$" should read -- $C_{20}$ --.
  Example No. 13, "$C_{28}$" should read -- $C_{20}$ --.
  Example No. 14, "$C_{28}$" should read -- $C_{20}$ --.
  Example No. 19, "$H_{38}$" should read -- $C_{30}$ --.
  Example No. 25, "$C_{28}$" should read -- $C_{20}$ --.

Columns 17 and 18, Table 4, under heading "Analysis for"
  Example No. 27, "$C_{22}$" should read -- $C_{21}$ --.
  Example No. 29, "$C_{28}$" should read -- $C_{20}$ --.
  Example No. 30, "$C_{22}$" should read -- $C_{21}$ --.
  Example No. 31, "$H_{23}$" should read -- $H_{28}$ --.

Columns 17 and 18, Table 4, under heading "(Calcd. C;H;N;, Found C;H;N;)", first column, Example 31, "97.72;" should read -- 67.72 --.

UNITED STATES PATENT AND TRADEMARK OFFICE
CERTIFICATE OF CORRECTION

PATENT NO. : 4,983,633

DATED : Jan. 8, 1991

INVENTOR(S) : Yasuo Itoh, Hideo Kato, Eiichi Koshinaka, Nobuo Ogawa, Hiroyuki Nishino, Jun Sakaguchi It is certified that error appears in the above-identified patent and that said Letters Patent is hereby corrected as shown below:

Column 17 and 18, Table 4, under heading "Analysis for"

Example No. 32; "$H_{38}$" should read -- $H_{30}$ --.

Example No. 33; "$H_{36}$" should read -- $H_{30}$ --.

Example No. 34; "$H_{25}$" should read -- $H_{26}$ --.

Example No. 38; "$H_{28}$" should read -- $H_{29}$ --.

Column 17/18, Table 4, under heading "melting point (solvent)",

Example 38, line 2; "MeOH" should read -- EtOH) --.

Column 17 and 18, Table 4, under heading "Analysis for"

Example No. 39; "$H_{25}$" should read -- $H_{26}$ --.

Example No. 41; "$H_{25}$" should read -- $H_{26}$ --.

Example No 42; "$H_{32}$" should read -- $H_{31}$ --

Example No. 43; "$C_{23}$" should read -- $C_{22}$ --

Column 19 and 20, Table 4, under heading "Analysis for",

Example No. 48, line 1; "$C_{18}$" should read -- $C_{19}$ --.

Example No. 48, line 3; "$C_{18}$" should read -- $C_{19}$ --.

Example No. 49; "$C_{18}$" should read -- $C_{20}$ --.

Example No. 50; "$H_{22}$" should read -- $H_{21}$ --.

Columns 19 and 20, Table 4, under heading "crystals",

Example 51, line 1; "yello2" should read -- yellow --.

Column 19 and 20, Table 4, under heading "Analysis for",

Example 51, line 1; "$H_{22}$" should read -- $H_{21}$ --.

Example 51, line 3; "$H_{22}$" should read -- $H_{21}$ --.

Example 52; "$H_{22}$" should read -- $H_{21}$ --.

Example 53, line 1; "$C_{18}H_{22}$" should read -- $C_{19}H_{21}$ --.

Example 53, line 3; "$C_{18}H_{22}$" should read -- $C_{19}H_{21}$ --.

UNITED STATES PATENT AND TRADEMARK OFFICE
CERTIFICATE OF CORRECTION

PATENT NO. : 4,983,633

DATED : Jan. 8, 1991

INVENTOR(S) : Yasuo Itoh, Hideo Kato, Eiichi Koshinaka, Nobuo Ogawa, Hiroyuki Nishino, Jun Sakaguchi It is certified that error appears in the above-identified patent and that said Letters Patent is hereby corrected as shown below:

Column 19 and 20, Table 4, under heading "Analysis for",
  Example No. 54; "$H_{38}$" should read -- $H_{30}$ --.
  Example No. 55; "$C_{28}$" should read -- $C_{20}$ --.
  Example No. 56; "$C_{22}H_{28}$" should read -- $C_{21}H_{26}$ --.
  Example No. 57; "$C_{22}$" should read -- $C_{21}$ --.

Column 19 and 20, Table 4, under Heading "$R_1$", Example No. 58;
  "3-$NO_3$" should read -- 3-$NO_2$ --.

Column 19 and 20, Table 4, under heading "Analysis for",
  Example No. 59, line 1; "$H_{28}$" should read -- $H_{20}$ --.
  Example No. 59, line 3; "$H_{28}$" should read -- $H_{20}$ --.
  Example No. 60; "$H_{28}$" should read -- $H_{20}$ --.

Column 21 and 22, Table 4, under heading "Analysis for",
  Example No. 61; "$H_{22}$" should read -- $H_{20}$ --.
  Example No. 62, line 1; "$H_{22}$" should read -- $H_{23}$ --.
  Example No. 62, line 3; "$H_{22}$" should read -- $H_{23}$ --.
  Example No. 63; "$C_{22}H_{28}$" should read -- $C_{21}H_{25}$ --.
  Example No. 65; "$C_{28}H_{28}$" should read -- $C_{20}H_{26}$ --.
  Example No. 68; "$H_{22}$" should read -- $H_{23}$ --.
  Example No. 70, line 1; "$H_{22}$" should read -- $H_{21}$ --.
  Example No. 70, line 3; "$H_{22}$" should read -- $H_{21}$ --.
  Example No. 71, line 1; "$H_{22}$" should read -- $H_{21}$ --.
  Example No. 71, line 3; "$H_{22}$" should read -- $H_{21}$ --.
  Example No. 72; $H_{22}$ should read -- $H_{23}$ --.

UNITED STATES PATENT AND TRADEMARK OFFICE
CERTIFICATE OF CORRECTION

PATENT NO. : 4,983,633

Page 4 of 4

DATED : Jan. 8, 1991

INVENTOR(S) : Yasuo Itoh, Hideo Kato, Eiichi Koshinaka, Nobuo Ogawa, Hiroyuki Nishino, Jun Sakaguchi It is certified that error appears in the above-identified patent and that said Letters Patent is hereby corrected as shown below:

Column 21 and 22, Table 4, under heading "Analysis for",
  Example No. 73; "$H_{22}$" should read -- $H_{23}$ --.
  Example No. 74, line 1; "$C_{18}H_{22}$" should read -- $C_{19}H_{21}$ --.
  Example No. 74, line 3; "$H_{22}$" should read -- $H_{21}$ --.
  Example No. 76, line 1; "$H_{22}$" should read -- $H_{21}$ --.
  Example No. 77; "$C_{28}H_{23}Cl_8$" should read -- $C_{20}H_{23}Cl_2$ --.

Column 25, line 3; after "-dimethoxybenzamide" insert -- and --.
  (R&A 5-16-90, P. 2)

Column 17 and 18, Table 4, under heading "Analysis for"
  Example No. 36; "$C_{26}$" should read -- $C_{20}$ --.

Signed and Sealed this

Twenty-fifth Day of February, 1992

Attest:

HARRY F. MANBECK, JR.

Attesting Officer

Commissioner of Patents and Trademarks